United States Patent [19]
Faulhaber

[11] 3,986,037
[45] Oct. 12, 1976

[54] YARN DETECTOR WITH A SELF-CALIBRATING CIRCUIT

[75] Inventor: Mark Edwin Faulhaber, Wilmington, Del.

[73] Assignee: E. I. Du Pont de Nemours and Company, Wilmington, Del.

[22] Filed: Oct. 3, 1975

[21] Appl. No.: 619,197

[52] U.S. Cl. .................. 250/562; 250/214 AG; 356/238
[51] Int. Cl.² ........................................ G01N 21/32
[58] Field of Search ........... 250/562, 563, 572, 559, 250/206, 214 R, 214 AG; 356/237, 238, 239; 28/64; 330/75, 86

[56] References Cited
UNITED STATES PATENTS

| | | | |
|---|---|---|---|
| 3,132,254 | 5/1964 | Woodward | 250/562 |
| 3,421,007 | 1/1969 | Schwartz | 250/214 |
| 3,887,814 | 6/1975 | Faulhaber | 356/238 |

Primary Examiner—David C. Nelms

[57] ABSTRACT

In a yarn inspection system for detecting variations in yarn diameter wherein a plurality of yarns move past a plurality of transducers for generating electrical signal outputs corresponding to yarn diameter and including discriminator circuitry sequentially connected to each of the transducers for processing the signal outputs, a self calibrating circuit arrangement has been devised to compensate for normal variations in the output of individual transducers due to different characteristics among the separate transducers.

2 Claims, 2 Drawing Figures

YARN DETECTOR WITH A SELF-CALIBRATING CIRCUIT

BACKGROUND OF THE INVENTION

This invention relates to apparatus for measuring variations in the diameter of textile yarns particularly those which are intentionally induced in the yarn and are frequently called slubs or "slugs". More specifically, this invention concerns electronic signal processing circuitry which is a modification of the apparatus taught by Faulhaber in U.S. Pat. No. 3,887,814.

In the commercial production of yarn, many separate positions are generally employed, each producing an individual end of yarn. Although it is often possible to sample yarn from packages made from these various positions and assess yarn quality after the yarn is produced, it has been found particularly important in connection with the manufacture of slub yarns to monitor the yarn quality continuously for each yarn position as it is being manufactured.

SUMMARY OF THE INVENTION

This invention is a modificaion of the single position yarn analyzer taught in the above-referenced patent which makes it possible to sequentially analyze yarn quality for a multiplicity of individual yarn ends as they are being produced in separate machine positions using a single yarn characterization instrument, i.e., electronic discriminator means. To do this a novel self-calibrating circuit arrangement has been devised to compensate for normal variations in output of individual yarn diameter sensors resulting from typical small temporal variations in their optical and mechanical characteristics. This self-calibration is achieved by modifications to the drift compensation and zero reference circuit 20 of U.S. Pat. No. 3,887,814 in order to make it an input ratioing zero self-calibration-referenced circuit. Ratioing nullifies the influence of differences in sensing head parameters when measuring the output signals from a series of individual optical yarn sensing heads for a given yarn diameter value passing each of the sensors.

More particularly, the invention resides in an electronic subcircuit for the self-calibration of a yarn inspection system wherein several separate yarn ends move at a uniform rate past respective individual transducer means for generating electronic signal outputs corresponding to instantaneous variations in the respective yarn diameters. A multiplexer provides sequential switching of these outputs in turn to the self-calibration subcircuit. This latter circuit includes a variable gain amplifier with an input, an output, and an automatic gain control (AGC) terminal and a summing amplifier having one of its terminals connected to the output terminal of the variable gain amplifier and to a reference voltage source in order to provide a resultant calibrated signal. An electronic switch having a control terminal is connected between the latter amplifier and an integrating amplifier which is arranged to provide a time average output when the electronic switch is closed. This output is connected to the AGC terminal of the first amplifier. The integrating amplifier maintains the time average output constant when the switch is opened. Discriminator circuitry responsive to the calibrated signal provides an indication signal and a switch control signal to the electronic switch when the calibrated signal exceeds a predetermined minimum threshold value. Additional integrating, discriminating and readout circuitry as described in U.S. Pat. No. 3,887,814 may also be added to the system of this present invention.

DETAILED DESCRIPTION OF THE PREFERRED EMBODIMENT

Figure 1:
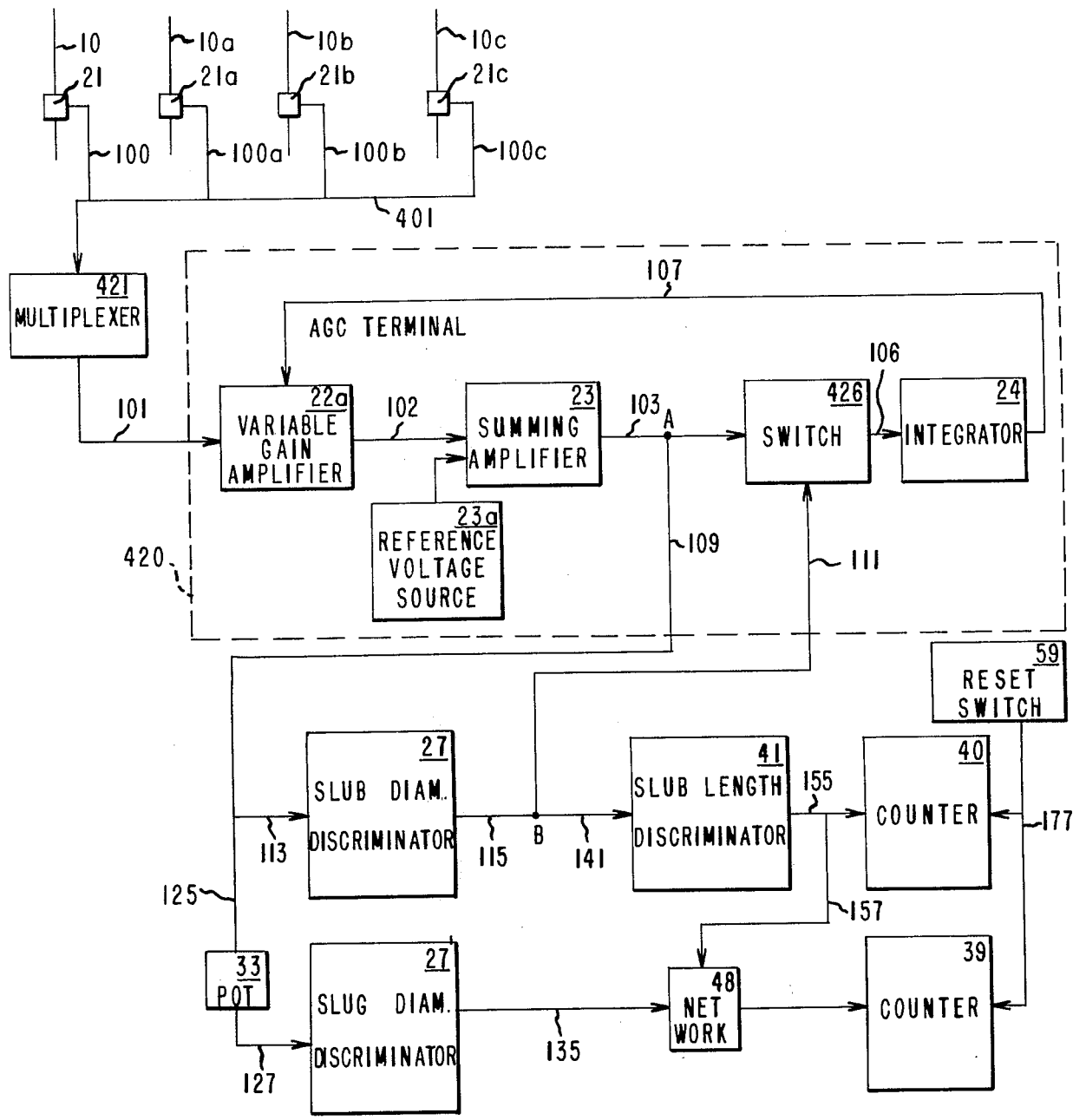
FIG. 1 is a schematic block diagram for a yarn diameter analyzer which includes the subcircuit of this invention.

Referring to FIG. 1 four yarn ends 10, 10a, 10b and 10c are passed at uniform rate through photoelectric transducers 21, 21a, 21b and 21c, respectively, by means not shown. Output electrical lines 100, 100a, 100b and 100c connect the transducers through cable 401 to the input side of multiplexer 421. In the preferred embodiment the transducers 21 are Loepfe Model FR30 optical transducers and the multiplexer 421 is a Model 606 manufactured by Vidar Corporation. The output of multiplexer 421 is connected over line 101 to the self-calibration-zero reference circuit 420 which includes a variable gain amplifier 22a connected to a summing amplifier 23 via line 102 which in turn is connected over line 103 past connector point A to the input terminal of electronic switch 426, the output of which extends over line 106 to integrator 24. The output of the latter is connected to line 107 and back to the AGC (automatic gain control) terminal of amplifier 22a. A reference voltage source 23a is connected to an input of amplifier 23. An output line 109 from point A in circuit 420 is first connected over line 113 to slub diameter discriminator 27. The output line 115 from discriminator 27 extends to a terminal B and thence over line 141 to slub length discriminator 41. Line 111 connects terminal B to the control terminal of switch 426. Discriminators 27 and 41 are the slub diameter and length discriminators, respectively, that are fully described in U.S. Pat. No. 3,887,814. Discriminator 41 is connected over line 155 to counter 40 and over line 157 to network 48. A second branch line 125 from output line 109 is connected to potentiometer 33 and thence over line 127 to slug diameter discriminator 27', the output of which extends over line 135 to an input terminal of network 48. The output of network 48 is connected to counter 39. A reset switch 59 is connected over branched line 177 to the reset terminals of counters 40 and 39.

Figure 2:
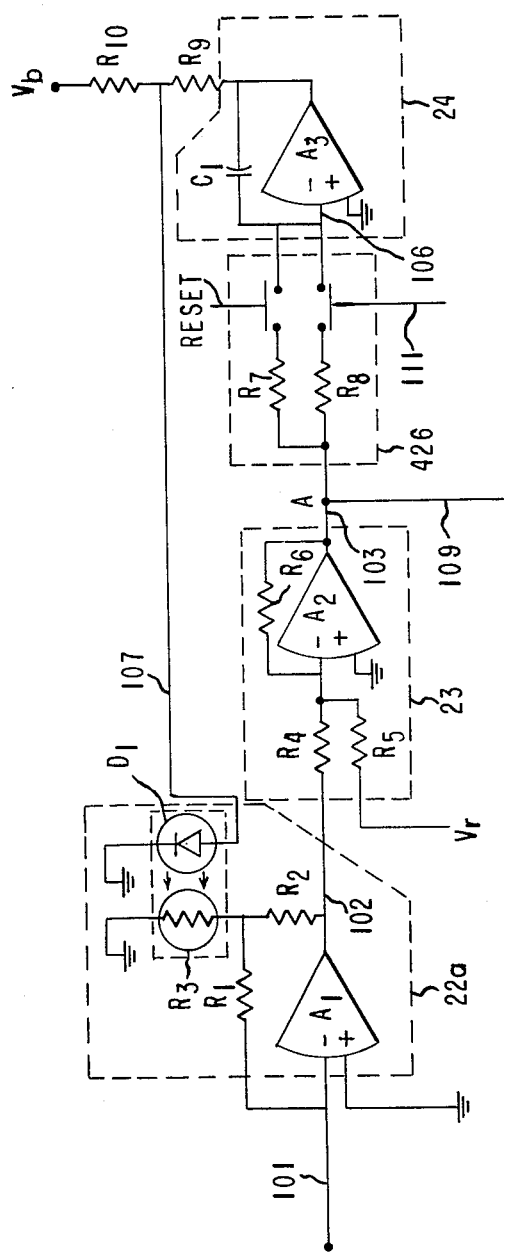
FIG. 2 is a circuit diagram for the novel subcircuit of this invention.

Details of the self-calibration-zero reference circuit are shown by the schematic circuit diagram of FIG. 2. Thus, the output line 101 from multiplexer 421 extends to the negative input terminal of a first operational amplifier $A_1$ which is typically a Teledyne-Philbrick Co., Model 1426. The positive input terminal is grounded and the output terminal is connected to line 102. Gain control properties are provided by a resistance network comprising fixed resistors $R_1$ and $R_2$ series connected in feedback between the output and input terminals of amplifier $A_1$ and resistor $R_3$ connected from the juncture of $R_1$ and $R_2$ to ground. $R_3$ is the photoconductive resistor part of an optical isolator, typically a Clairex Co. Type CLM6000. This isolator provides a transfer of signals from line 107. Line 107 extends from the output of integrator circuit 24 and carries a feedback current which activates and determines the amount of light produced in the light emitting diode $D_1$, the other element of the optical isolator. The magnitude of this feedback current is determined by the combination of the output voltage level of integrator 24 through resistor $R_9$ and a bias voltage $V_b$ applied to resistor $R_{10}$. Amplifier $A_1$ along with the gain control network forms the variable gain amplifier 22a of FIG. 1. The output from amplifier 22a is connected over line 102 through an input resistor $R_4$ to the negative input terminal of a second operational amplifier $A_2$. A reference voltage Vr from source 23a (FIG. 1) of opposite polarity to the output from 22a is connected through an input resistor $R_5$ to the same terminal of $A_2$. The positive input of $A_2$ is grounded. A feedback resistor $R_6$ is connected around the input and output terminals of amplifier $A_2$. This amplifier and its associated feedback and input resistors comprise the summing amplifier 23 of FIG. 1. The output of amplifier 23 extends over line 103 through a terminal A and to one side of switch 426 which comprises in effect, a solid-state switch which includes two input branches, one having input resistor $R_7$ and the other input resistor $R_8$ connected to a Siliconix dual FET electronic switch type DG200BA. Control line marked "reset" for the $R_7$ branch of switch 426 is used to change the integrator rate ($R_7 << R_8$) for rapid recalibration when multiplexing to the next transducer. The control terminal for the $R_8$ branch is connected to line 111. Both switch output sides are connected to line 106. Line 106 then connects to the input side of integrator 24, specifically to the negative terminal of a third operational amplifier $A_3$. This amplifier has capacitor C1 connected in feedback between input and output terminals. The output from amplifier $A_3$ is connected through resistor $R_9$ to feedback line 107. A fixed voltage power source $V_b$ is connected through resistor $R_{10}$ also to line 107. Amplifiers $A_2$ and $A_3$ are typically models 1426 from Teledyne-Philbrick Co.

In the operation of this self-calibration-zero reference circuit 420, amplifier 22a accepts a transducer signal $I_y$ and since it is an inverting amplifier, produces a negative voltage, $-V_y$, which then is summed with a positive reference voltage Vr so that amplifier 23 which is also an inverting amplifier provides an output voltage $K(V_y-V_r)$ where K is the gain of this amplifier. This amplified sum is integrated in integrator circuit 24 and then fed back as an automatic gain control (AGC) signal to adjust the gain G of amplifier 22a forcing this gain to change until the value of $K(V_y-V_r)$ equals zero, at point A. When this occurs the transducer signal is calibrated. Calibration occurs automatically while a section of yarn having no slubs (i.e., of substantially constant diameter) is passed through the particular transducer then connected by the multiplexer into the circuit. When unslubbed yarn is passing through the transducer the average voltage at point A is zero. If a slub or other increased yarn diameter section passes through the transducer, the shadow cast on the photodetector increases which decreases the output current $I_y$ of that transducer. This produces a negative voltage at A (since as previously taught in the referenced patent, the time constant of integrator 24 is chosen to be slower than the slub events of interest). This voltage at A appears on line 109 and is applicable to operate the discriminator circuit 27 of FIG. 1 and provide a control signal at point B which is fed over line 111 to operate switch 426. This switch removes the input signal to integrator 24 and causes it to hold its output level at the value attained for unslubbed yarn. This is a relatively long term average value and in this way this circuit provides a stable reference level at zero representating the average yarn diameter exclusive of slubs and other large diameter excursions.

That a self-calibration results is understood from the following analysis. A Loepfe FR30 optical transducer 21 provides an electrical output signal proportional to the diameter of yarn passing through it. Basically, the transducer contains a light source producing light and by use of a light pipe, forms a light beam having an essentially rectangular cross section which is directed toward a silicon cell photodetector. The yarn is guided through the light beam. With no yarn in the transducer, the photodetector receives all the light. When yarn is present, a shadow whose area is proportional to the yarn diameter is present on the photodetector.

The signal produced by the photodetector with no yarn present is described by the following equation:

$$I = LTSWH \tag{1}$$

where
$I$ = photodetector current
$L$ = light source intensity
$T$ = light pipe transmittance
$S$ = photodetector sensitivity
$W$ = beam width in direction of yarn travel, and
$H$ = beam width in direction of yarn diameter.

When a yarn bundle having a diameter, $d$, is placed in the optical path, the signal $I_y$ becomes:

$$I_y = LTS\,W(H-d) \tag{2}$$

where it is seen that the initial signal is reduced by the area of the yarn bundle shadow ($Wd$). This equation can also be written:

$$I_y = (LTS)(WH)(1-d/H) \tag{2a}$$

From this latter equation (2a) it can be seen that the signal current is determined by transducer electro-optical factors ($L$, $T$, $S$), mechanical design factors ($W$, $H$) and the measurement of interest ($d$). Each transducer can be expected to produce a particular signal due to its electro-optical ($L$, $T$, $S$) characteristics and these will differ from one transducer to another. In addition, any transducer can be expected to change its sensitivity as its light source dims, or the photodetector ages or changes sensitivity with ambient temperature, or the path transmittance changes caused by dust or oil deposits or light pipe yellowing. Factors less likely to vary widely or change significantly are the mechanical factors, the beam cross-sectional dimensions ($W$, $H$).

The self-calibration action will be more clearly understood by considering the following circuit analysis.

With switch 426 permitting signals to pass to integrator 24 and with normal unslubbed yarn in the transducer head:

$$-V_y = GI_y = G(LTS)(WH)(1-d_o/H) \tag{3}$$

where $d_o$ is the normal unslubbed yarn diameter and $G$ is the gain of amplifier 22a.

As described, the feedback circuit causes $$V_y - V_r = 0 \text{ or } V_y = V_r$$

Therefore, $$-V_r = G(LTS)(WH)(1-d_o/H) \qquad (4)$$

and the gain, $G$, of variable gain amplifier 22a can be expressed as $$G = \frac{-V_r}{(LTS)(WH)(1-d_o/H)} \qquad (5)$$

When a slub with a diameter, $d_s$, passes through the transducer head, the gain $G$ does not change because switch 426 opens the circit to integrator 24a holding the integrator value being fed back to 22a as an AGC signal at the "pre-slub" value. Now, the transducer signal during a slub event $I_s$ becomes:

$$I_s = (LTS)(WH)(1-d_s/H) \qquad (6)$$

and since $-V_s = GI_s$, then substituting for $G$ from (5) gives $$V_s = \frac{V_r}{(LTS)(WH)(1-d_o/H)} \times (LTS)(WH)(1-d_s/H) \qquad (7)$$

$$\text{or } V_s = \frac{V_r(1-d_s/H)}{(1-d_o/H)} \qquad (7a)$$

Thus, $V_s$ is independent of the electro-optical factors ($LTS$).

The output, $V_o$, of summing amplifier 23a during a slub event will be $$V_o = K(V_s - V_r)$$
$$\qquad (8)$$

and thus $$V_o = K\left[\frac{(V_r(1-d_s/H))}{(1-d_o/H)} - V_r\right] \qquad (8a)$$

which reduces to $$V_o = -KV_r\left(\frac{d_s-d_o}{H-d_o}\right) \qquad (8b)$$

Note that the only remaining transducer factor which could vary from one transducer to another is the beam width H in the direction of the yarn diameter. If, for a given feed yarn normal diameter, the average measured diameter, $d_o$, which will be substantially constant is much smaller than $H$ (e.g., for 120 denier yarn, $d_o \sim 0.02\ H$), the differences in $H$ among transducers can be compensated for by making $V_r/H$ a constant. In practice a value $V_r/H = 5$ was used. This permits $V_r$ to be adjusted the small amount required to account for the variations in H among the multiplexed transducers. In the preferred embodiment a digital computer is used to program the individual corrections to $V_r$ for individual values of $H$. Correction is accomplished through a digital to analog converter means (not shown) connected as a control input to voltage source 23a of FIG. 1 for maintaining $V_r/H$ constant.

The general equation for any of the multiplexed transducers when the gain $K$ of amplifier 23 is 4 then becomes effectively $$V_o = -20(d_s-d_o). \qquad (9)$$

The average value of $V_o$ will be zero for normal feed yarn. Slubs are measured with respect to the base yarn diameter with a sensitivity (at the indicated gain) of about 0.1 volts/mil. This is more than adequate to ensure consistent slub and slug detection and does not require unusual performance from any circuit components.

Thus, a yarn diameter monitoring system of the type described in U.S. Pat. No. 3,887,814 has been modified in a novel way to provide not only for sequentially analyzing the diameter variability of a multiplicity of separate yarn ends but also to provide self-calibration characteristics which compensate for variability among yarn diameter transducers due to differences in design factors and compensates for temporal changes in the conversion efficiency of each transducer with time such as by accumulation of dust or ageing of optical light source and detector components.

In the preferred embodiment, the readout system takes the form of a conventional printout apparatus which sequentially prints out the yarn characteristics after each individual yarn transducer has been connected into the circuit by means of the multiplexer circuit.

What is claimed is:

1. In a yarn inspection system for detecting variations in yarn diameter wherein a yarn moves past a transducer for generating electrical signal outputs corresponding to yarn diameter and including electronic discriminator means connected to said transducer for processing said electrical signal outputs to indicate variations above a predetermined level, the improvement comprising: a variable gain amplifier circuit responsive to said electrical signal outputs for supplying a voltage output; a means summing the voltage output from the variable gain amplifier with a reference voltage of opposite polarity for supplying a resultant signal to said electronic discriminator means; means for automatically adjusting the gain of the amplifier to maintain the output of said amplifier at a constant level when yarn of substantially constant diameter is passing through the transducers; and means actuated by said discriminator means for maintaining the gain of said amplifier at a constant level when instantaneous variations in yarn diameter occur above a predetermined level.

2. The system as defined in claim 1, there being a plurality of yarns moving past a plurality of transducers, each of said transducers being sequentially connected to said electronic discriminator means for processing electrical signal outputs from each transducer.

* * * * *